United States Patent [19]

Provonchee et al.

[11] Patent Number: 4,659,672
[45] Date of Patent: Apr. 21, 1987

[54] COLONY REPLICATING DEVICE

[75] Inventors: Richard B. Provonchee, Camden; Donald W. Renn, Glen Cove, both of Me.

[73] Assignee: FMC Corporation, Philadelphia, Pa.

[21] Appl. No.: 345,966

[22] Filed: Feb. 5, 1982

[51] Int. Cl.⁴ ............................................. C12M 1/00
[52] U.S. Cl. .................................. 435/287; 435/299
[58] Field of Search ............... 128/759; 604/358, 385, 604/386; 435/287

[56] References Cited

U.S. PATENT DOCUMENTS

| | | | |
|---|---|---|---|
| 3,512,518 | 5/1970 | Mishkin et al. | 128/759 X |
| 3,684,660 | 8/1972 | Kereluk et al. | 435/294 |
| 3,751,341 | 8/1973 | Seitz et al. | 435/294 |
| 3,996,934 | 12/1976 | Zaffaroni et al. | 604/386 X |
| 4,368,272 | 1/1983 | Kashket | 435/287 |

*Primary Examiner*—Ferris H. Lander
*Attorney, Agent, or Firm*—Eugene G. Horsky; Christopher Egolf

[57] ABSTRACT

A device for replicating microbial or other cell colonies or aggregates comprises a layer of moisture absorbent material either in the form of a coherent film or comprising individual particles or a combination of film and particles, said layer being secured to a suitable handle forming element by means of which the device may be manipulated.

1 Claim, 8 Drawing Figures

U.S. Patent   Apr. 21, 1987   4,659,672

COLONY REPLICATING DEVICE

This invention relates to an improved device for replicating or transferring microbial or other cell colonies or aggregates from one culture growth medium to another and particularly to such a device which may be used to efficiently and faithfully transfer colonies from a first growth medium to a multiplicity of other media, which may be the same or different composition.

A frequent chore in certain types of microbiological and cell culture work involves the transfer of microbiological or cell colonies from one plate or dish of growth medium such as agar to other plates containing the same or different growth media. This is known as replica plating and is used to, among other things, facilitate routine tests involving repetitive inoculations of many isolates on the same or different media. While it is possible to perform replica plating by laboriously transferring one colony at a time, the current and most widely used method of transferring colonies while maintaining spatial integrity is the velvet pad method developed in about 1951 by Joshua and Esther Lederberg at the University of Wisconsin. With the velvet pad method, a piece of velvet fabric is wrapped snugly about the end of a cylindrical wood or cork support with the nap or pile facing outward. The fabric is held in place by a metal flange or hoop pushed over the fabric and around the rim of the support. After being sterilized, the end of the cylinder with its velvet cover is contacted with the agar plate carrying the initial colonies with light pressure to transfer the colonies by imprinting them on the velvet. Subsequent engagement of the velvet covered end of the cylinder with other growth media causes the colonies to be replicated thereon in the same spatial configuration as on the mother plate. While there are other devices used for this purpose, the velvet pad method is believed to be the closest prior art.

There are a number of shortcomings to the velvet pad method; notably, the pad has a tendency to smudge colonies after only a few replicates and is not very effective at picking up and transferring small colonies.

The present invention is directed toward a colony replicating device which is capable of faithfully producing a large number of replicates.

The device is susceptible to many specific embodiments, a few more simple forms of which are diagrammatically illustrated on the accompanying drawing wherein.

Figure 1:
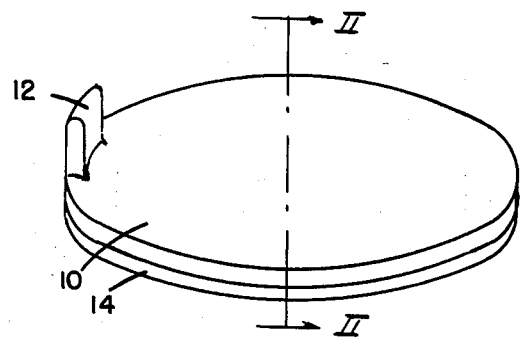
FIG. 1 is a perspective view of one form of the device.

Essentially, the device comprises a moisture absorbent material carried by some kind of support by means of which it may be manipulated. In FIGS. 1-5 the support or manipulatable means consists of a member 10 which is preferably a relatively stiff but flexible film. The amount of stiffness of the film need only be such that it is not limp. Thus, member 10 should normally be stiff enough that it cannot be folded flat upon itself without breaking or permanently creasing. It is also preferable that member 10 be transparent. To further facilitate manipulation of the device, member 10 is provided with a tab 12 which serves as a handle. In FIG. 1, tab 12 is shown as integral with member 10 but if desired it may be a separate piece suitably secured to member 10. Member 10 is made in the shape and size of the petri dishes in connection with which it is to be used. Usually this will be circular, but sometimes other shapes may be employed. In order to permit the device to contact the entire surface of the medium in the petri dish, tab 12 should not extend beyond the periphery of member 10. When the tab is integral with member 10 it is folded back away from the edge of said member.

In order to facilitate adhesion of the moisture absorbent material to member 10 at least one surface thereof should preferably be hydrophilic. If member 10 is a plastic film such as polyester or polyethylene teraphthalate, one surface may be rendered hydrophilic by any of various well-known methods such as a corona discharge.

Figure 2:
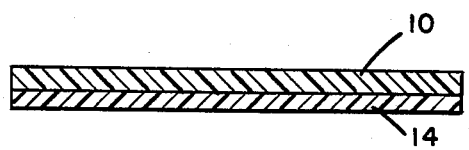
FIG. 2 is a cross-sectional view taken along the line II—II of FIG. 1.

In that form of the device shown in FIGS. 1 and 2, the moisture absorbent material used for picking up and transferring the cell colonies is in the form of a smooth film 14 which may be cast upon the hydrophilic surface of member 10 or may be suitably adhered thereto after having been formed as a self-supporting film. A variety of materials and combinations thereof may be used to form film 14. Suitable materials are natural hydrocolloids, for example, galactomannans such as locust bean gum, guar gum and tara gum. Other suitable natural materials are calcium alginate, collagen, gelatin, and polymers such as kappa and lambda carrageenan. Certain semi-synthetic derivatives of hydrocolloids such as starch and cellulose graft copolymers are also useful, as are hydroxyethyl derivatives of agar and agarose. A starch graft copolymer known generically as "super slurper" is particularly effective for use as film 14. Reference is directed to U.S. Pat. No. 3,935,099 for one example of "super slurper". Also useful are fully synthetic water insoluble hydrocolloids such as polyacrylamide, polyvinyl alcohol, polyethylene glycol and polyethylene oxides. Absorbent films of any of the foregoing may also contain non-polymeric components such as nutrient media, non-toxic surfactants and/or humectants to keep the film flexible.

In use, the device of FIGS. 1 and 2 is manipulated by the tab 12 to bring absorbent film 14 into contact with the cell colonies on the mother growth medium. The colonies adhere to the absorbent film 14 and the device with the colonies adhered thereto is lifted from the original growth medium and brought successively into contact with other growth media, during each of which subsequent contacts a portion of each colony is transferred to or replicated upon the new medium. The absorbent film 14 serves to effect more faithful replicates that are normally achieved by the previously known velvet pad, as well as more of them. When support member 10 is transparent, the operator is able to observe the replicating process and make sure that the device contacts and transfers all desired colonies.

Figure 3:
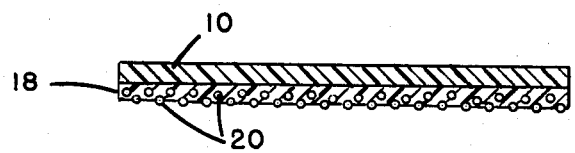
FIG. 3 is a cross-sectional view of a modified form of the device.

Since all colonies and aggregates are not of uniform height, it is sometimes desirable that the replicating medium not have a smooth even surface as does film 14 but instead have an irregular or non-planar surface so that contact may be made better with those portions of the cell colonies which may not be as high as others. Such an irregular or uneven surface may be provided in various ways such as by embedding small particles of absorbent material in the overall absorbent film, or by a film of absorbent material on a preformed irregular "bumpy" plastic surface. Roughness may also be provided by non-asorbent additives such as fine silica particles in an absorbent film. One such form of the device is shown in FIG. 3 wherein the overall absorbent film is indicated at 18 and the particles of absorbent material at 20. The overall absorbent film 18 may be formed of any of the materials referred to above in connection with the film 14 as may also be the particles 20. Particles 20 may be cut from preformed film or may be granules. In this form of the invention, film 18 is cast on support 10 and the particles 20 are sprinkled on or pressed into the film before the film is firmly set.

Figure 4:
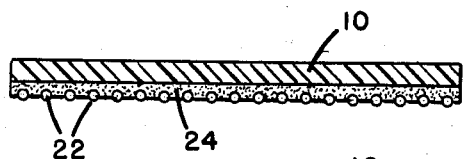
FIG. 4 is a cross-sectional view of another modification.

In the form of device shown in FIG. 4, absorbent particles 22 are embedded in a layer of adhesive 24 by means of which they are secured to the support member 10.

Figure 5:
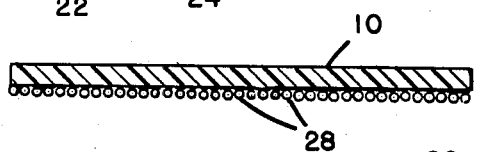
FIG. 5 is a cross-sectional view of still another modification.

In that modification shown on FIG. 5, absorbent particles 28 are individually adhesively secured to the support member 10.

In those forms of the device shown in FIGS. 4 and 5, the absorbent particles are formed of the same material as described above in connection with film 14.

Figure 6:
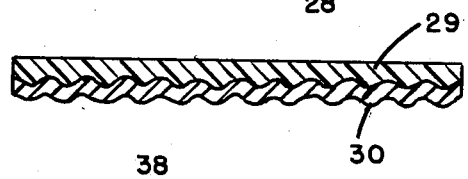
FIG. 6 is a cross-sectional view of yet another modification.

In FIG. 6 the support is indicated at 29 and is shown as having an irregular or bumpy surface to which is adhered an absorbent film 30 which is of substantially uniform thickness and consequently also has an irregular or bumpy surface. Except for its irregular surface, support 29 is identical with support 10 and the absorbent film 30 is the same composition as film 14.

Figure 7:
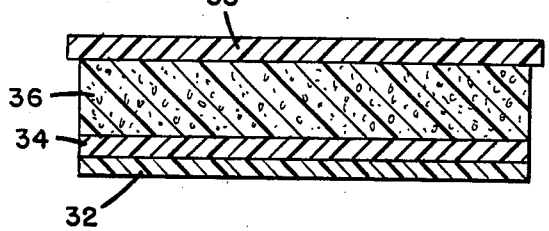
FIG. 7 is a cross-sectional view of another embodiment of the invention.
Figure 8:
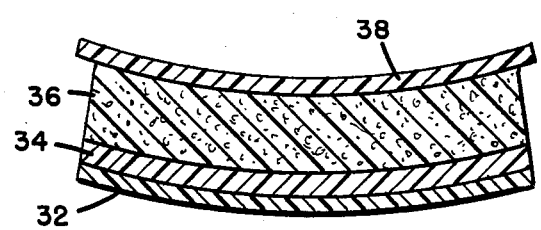
FIG. 8 is a cross-sectional view showing the embodiment of FIG. 7 as manipulated during use.

FIGS. 7 and 8 illustrate a form of the replicating device which may be found to be somewhat more convenient to operate. In this form, the absorbent material or replicating layer is indicated at 32 and the support member at 34. Support member 34 is the same as support member 10 except that it is not provided with a tab such as tab 12. Absorbent material 32 may be in any of those forms and materials previously described in connection with FIGS. 1 through 5.

Support member 34 is adhesively secured to a resilient pad 36 preferably but not necessarily formed of polyurethane foam. As shown in the drawing, pad 36 has two parallel flat faces one of which is secured to member 34 and the other of which is secured to a handle forming means 38.

Handle forming means 38 is a relatively stiff but somewhat flexible planar member such as for example a polyester film. The handle forming means 38 is somewhat larger than pad 36 and member 34 and when said handle forming means is grasped between the thumb and middle finger and squeezed while applying downward pressure with the index finger the entire device may be readily flexed a shown in FIG. 8. This flexing of the pad to make the replicating layer 32 convel enables the device to be brought into engagement with the growth medium with a minimum entrapment of air which generally results when two flat surfaces are brought together. After the convex surface makes contact with a medium, the flexing pressure is released so that the entire film or layer 32 uniformly engages the growth medium and due to the moisture absorption quality thereof, the colonies growing on the medium are picked up by the film. The device is again flexed when removing it to avoid the formation of a vacuum between the growth medium and the layer 32. Each time the device is contacted with and removed from a replicating plate, the flexing is repeated.

The device is made in the shape of the petri dishes with which it is to be used, usually circular. It is of a size such that the replicating layer 32 will cover substanially the entire surface of the growth medium. Pad 36 is made thick enough so that when layer 32 is resting on the medium, the handle forming member 38 will be above the edge of the petri dish and thus facilitate manipulation of the device.

As heretofore mentioned, the invention is susceptible to many specific embodiments and it is to be understood that the scope of the invention is limited only by the reasonable interpretation of the appended claims.

Having thus described the invention, what is claimed is:

1. A device for replicating bacterial or other cell colonies comprising a layer formed of hydrocolloid material having an exposed surface which, when contacted with a cell colony, absorbs moisture therefrom and into said layer and thereby picks up the colony on such surface, and means to which said layer is attached at a location remote from its exposed surface for use in manipulating said device into contact with a colony and during subsequent formation of replicates therof, wherein said means for manipulating said device includes a resilient pad, a pair of relatively moisture-impervious, self-supporting, flexible planar members, and means securing said planar members to opposite sides of said resilient pad with opposing surfaces thereof in substantially parallel relationship, one of said planar members having the layer of hydrocolloid material attached thereto and the other of said planar members facilitating the flexing of the device to impart a convex contour to said layer prior to and after contact with a colony and during replication to thereby minimize air entrapment or vacuum formation between said layer and the surface with which it is contacted.

* * * * *